United States Patent [19]

Walker et al.

[11] Patent Number: 4,910,204
[45] Date of Patent: Mar. 20, 1990

[54] 2-AMINO-5-HYDROXY-4-PYRIMIDONES

[75] Inventors: Frederick J. Walker, Preston; John L. LaMattina, Ledyard; Brian T. O'Neill, Westbrook, all of Conn.

[73] Assignee: Pfizer Inc., New York, N.Y.

[21] Appl. No.: 212,624

[22] Filed: Jun. 28, 1988

[51] Int. Cl.$^4$ .............. A61K 31/505; A61K 31/445; C07D 239/22
[52] U.S. Cl. .................... 514/272; 514/273; 514/825; 514/826; 514/863; 514/925; 544/320; 544/321
[58] Field of Search ............... 544/320, 321; 514/272, 514/273, 825, 826, 863, 925

[56] References Cited

U.S. PATENT DOCUMENTS

| | | | |
|---|---|---|---|
| 4,153,793 | 5/1979 | Durant et al. | 544/320 |
| 4,416,885 | 11/1983 | Huvé | 514/272 |
| 4,535,080 | 8/1985 | Audiau et al. | 514/255 |
| 4,554,276 | 11/1985 | LaMiattina | 544/298 |
| 4,694,008 | 9/1987 | Brown et al. | 514/269 |

FOREIGN PATENT DOCUMENTS

| | | |
|---|---|---|
| 0063509 | 10/1982 | European Pat. Off. |
| 0138464 | 4/1985 | European Pat. Off. |
| 0180298 | 5/1986 | European Pat. Off. |
| 3009071 | 9/1980 | Fed. Rep. of Germany |
| 3436380 | 4/1986 | Fed. Rep. of Germany |
| 61-205260 | 11/1986 | Japan |
| 756189 | 8/1956 | United Kingdom |

OTHER PUBLICATIONS

Lazarev et al, CA 67-72356b (1967) "Effect of some pyrimidine derivatives on the blastomogenis ...".
Asadov, CA 70-2232w (1969) "Effect of 4-methylisocytosine and 5-hydroxy-4-methyisocytosine ...".
Miller et al. CA 78-54733v (1973) "Guanine phosphoribosyltransferase from Escherichia coli.".
Oda et al, CA 79-66309v (1973) "Synthesis of compounds related to antitumor agents. I".
Plechev. CA 80-22502u (1974) "Stimulation with some pyrimidine derivatives of ...".
Plechov CA 85-116661a (1976) "Stimulation of the absorbent capacity of ...".
Plechev, CA 87-127456e (1977) "Effect of some pyrimidine deriviatives on the ...".
Wierenpa et al, CA 95-43025r (1981) "Synthesis of 2-amino-6-phenyl-4(3H)-pyrimidinone-1-oxide".
Sako et al, CA 102-6373v (1985) "A versatile and convenient method for the synthesis ...".
LaMattina, Tetrahedron Letters, vol. 24, No. 20, pp. 2059-2062 (1988).
Jakschick, Prostaglandins, vol. 16, No. 5, pp. 733-747 (1978).
Hull, J. Chem. Soc., pp. 2033-2035 (1956).
LaMattina, Tetrahedron, vol. 44, No. 11, pp. 3073-3078 (1988).
Lasarev et al., Vop. Onkol, 13(7), 56-9 (1967).
Perchonock et al., Drugs of the Future, 12(9), 871-889 (1987).
Payne, Brit. Med. Journal, 295, 1138-1140 (1987).
Dale, Textbook of Immunopharmacology, 137-139 (1984).

Primary Examiner—Cecilia Shen
Attorney, Agent, or Firm—Peter C. Richardson; Paul H. Ginsburg; Karen DeBenedictis

[57] ABSTRACT

A compound of the formula

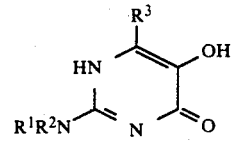

I or a pharmaceutically acceptable salt thereof, wherein $R^1$ is hydrogen; $R^2$ is ($C_1$-$C_{15}$) alkyl, ($C_3$-$C_{15}$)alkenyl, phenyl, substituted phenyl, ($C_7$-$C_{20}$)-phenylalkyl, or substituted ($C_7$-$C_{20}$)phenylalkyl wherein the substituents on the substituted phenyl and substituted phenylalkyl are independently one or two of fluoro, chloro, ($C_1$-$C_3$)alkyl, ($C_1$-$C_3$alkoxy, and trifluoromethyl; or $R^1$ and $R^2$ together with the nitrogen atom to which they are attached form a pyrrolodinyl, substituted pyrrolidinyl, piperidyl or substituted piperidyl group, wherein the substituents on said substituted pyrrolidinyl and piperidyl groups are independently one of ($C_1$-$C_6$)alkyl, phenyl, and ($C_7$-$C_9$)phenylalkyl; and $R^3$ is hydrogen, ($C_1$-$C_6$)alkyl, phenyl, substituted phenyl, ($C_7$-$C_9$)phenylalkyl, or substituted ($C_7$-$C_9$)phenylalkyl, wherein the substituents on the substituted phenyl and substituted phenylalkyl are independently one or two of fluoro, chloro, ($C_1$-$C_3$)alkyl, ($C_1$-$C_3$)alkoxy, and trifluoromethyl.

The compounds are useful in treating inflammation or other leukotriene mediated diseases, including plumonary, asthmatic, allergic, and gastrointestinal diseases.

26 Claims, No Drawings

2-AMINO-5-HYDROXY-4-PYRIMIDONES

The present invention relates to 2-amino-5-hydroxy-4-pyrimidones, pharmaceutical compositions comprising such compounds and the use of such compounds in treating inflammation or other leukotriene mediated diseases, including pulmonary, asthmatic, allergic, and gastrointestinal diseases.

European Patent Application Publication No. 0 180 298 refers to other 2-amino-5-hydroxy-4-pyrimidones that are stated to be useful as histamine $H_2$-antagonists.

The present invention relates to a compound of the formula

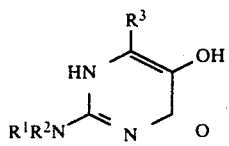

I or a pharmaceutically acceptable salt thereof, wherein $R^1$ is hydrogen; $R^2$ is $(C_1-C_{15})$alkyl, $(C_3-C_{15})$alkenyl, phenyl, substituted phenyl, $(C_7-C_{20})$phenylalkyl, or substituted $(C_7-C_{20})$phenylalkyl wherein the substituents on the substituted phenyl and substituted phenylalkyl, are independently one or two of fluoro, chloro, $(C_1-C_3)$alkyl, $(C_1-C_3)$alkoxy, and trifluoromethyl; or $R^1$ and $R^2$ together with the nitrogen atom to which they are attached form a pyrrolidinyl, substituted pyrrolidinyl, piperidyl or substituted piperidyl group, wherein the substituents on said substituted pyrrolidinyl and piperidyl groups are independently one of $(C_1-C_6)$alkyl, phenyl, and $(C_7-C_9)$phenylalkyl; and $R^3$ is $(C_1-C_6)$alkyl, phenyl, substituted phenyl, $(C_7-C_9)$phenylalkyl, or substituted $(C_7-C_9)$phenylalkyl, wherein the substituents on the substituted phenyl and substituted phenylalkyl are independently one or two of fluoro, chloro, $(C_1-C_3)$alkyl, $(C_1-C_3)$alkoxy, and trifluoromethyl.

The present invention also relates to a pharmaceutical composition useful in the treatment of leukotriene mediated diseases, including inflammation, comprising an amount of a compound of the formula I effective to treat a leukotriene mediated disease and a pharmaceutically acceptable carrier.

The present carrier also relates to a method of treating a leukotriene mediated disease (for example, inflammation) comprising administering to a patient in need of such treatment a compound of formula I in an amount effective to treat such disease.

Unless otherwise indicated, the alkyl groups of the compounds referred to herein (e.g. when $R^2$ of the compound of the formula I is $(C_1-C_{15})$alkyl), portions of such alkyl groups and the alkyl portions of other groups (e.g., alkenyl or phenylalkyl) referred to herein may be linear, branched or cyclic. Examples of cyclic alkyl groups include cyclopentyl and cyclohexyl.

A preferred embodiment of the invention relates to compounds of the formula I wherein $R^1$ is hydrogen; $R^2$ is linear or branched $(C_1-C_{15})$alkyl or $(C_7-C_{20})$phenylalkyl wherein the alkyl moiety is linear or branched; and $R^3$ is hydrogen or methyl. In a more preferred embodiment, $R^1$ is hydrogen, $R^2$ is methylheptyl and $R^3$ is hydrogen. Another preferred embodiment relates to compounds of the formula I wherein $R^1$ is heptyl, $R^2$ is hydrogen and $R^3$ is methyl.

Specific preferred compounds of the present invention include the following:
2-heptylamino-5-hydroxy-6-methyl-4-pyrimidone;
2-(6-methylheptyl-2-amino)-5-hydroxy-4-pyrimidone;
2-[(1-methyl-3-phenyl)-propyl]amino-5-hydroxy-4-pyrimidone; and
2-benzylamino-5-hydroxy-4-pyrimidone.

Other compounds of the present invention include 5-hydroxy-6-methyl-2-phenylhexylamino-4-pyrimidone and
5-hydroxy-6-methyl-2-phenylpropylamino-4-pyrimidone.

Compounds of the formula I wherein $R^3$ is hydrogen may be prepared as shown below in Scheme 1, which is discussed in detail below.

Scheme 1

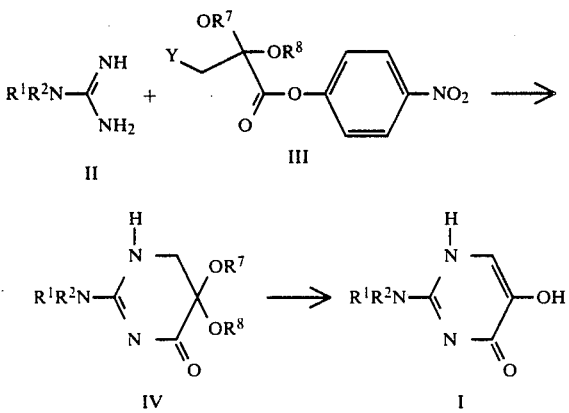

In order to prepare compounds of the formula I wherein $R^3$ is hydrogen, a compound of the formula II, wherein $R^1$ and $R^2$ are as defined above, is reacted with a compound of the formula III (prepared as described by J. LaMattina, *Tetrahedron Letters*, 2053 (1983)), wherein Y is chloro, bromo or iodo, preferably bromo, and $R^7$ and $R^8$ are independently selected from $C_1-C_4$ alkyl (e.g., ethyl), in a polar protic solvent, under an inert atmosphere, in the presence of an inorganic base (e.g., sodium hydroxide, potassium hydroxide or sodium hydride) or a strong organic base (e.g., sodium ethoxide or potassium tert-butoxide), at a temperature of about 0° to about 100° C. The preferred base is sodium ethoxide. The reaction mixture is preferably maintained at a temperature of about 25° C. for about 30 minutes to about 24 hours, more preferably for about 1 hour. Preferred solvents are $C_1$ to $C_4$ alcohols. The resulting compound of the formula IV is reacted with an acid catalyst (e.g., hydrochloric acid) in a polar protic solvent at a temperature of about 0° to 100° C. (preferably, about 60° C.) for about 4 to about 48 hours to provide a compound of the formula I. Preferably, the acid catalyzed reaction is carried out in neat formic acid.

Compounds of the formula I wherein $R^3$ is other than hydrogen may be prepared as shown in Scheme 2, which is discussed in detail below.

Scheme 2

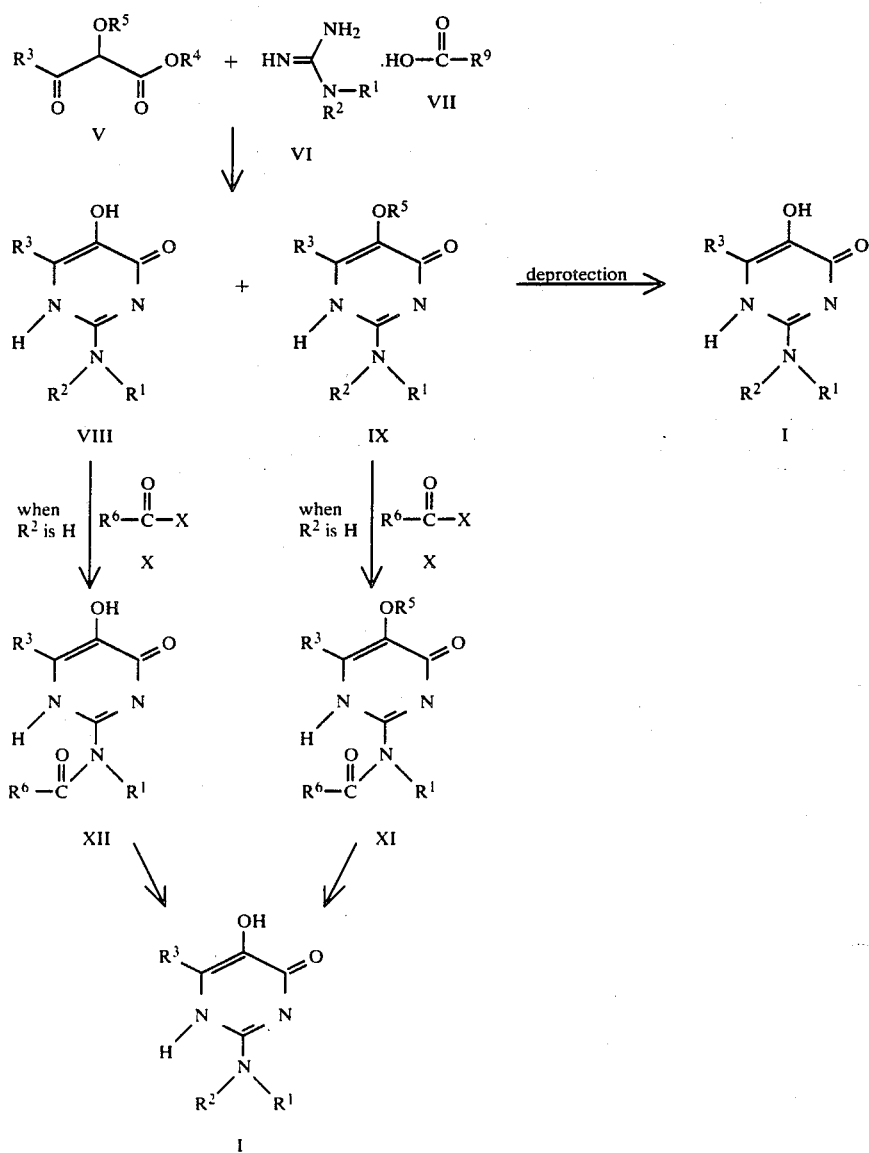

A compound of the formula V wherein $R^3$ is as defined for formula I, $R^4$ is $C_1$–$C_4$ alkyl, and $R^5$ is a protecting group

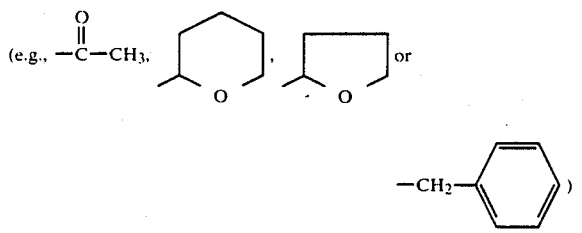

is reacted with a guanidine salt of the compound of the formula VI (e.g., a salt formed by the compound of the formula VI with a compound of the formula VII wherein $R^9$ is $C_1$–$C_4$ alkyl), preferably an acetate salt. The foregoing reaction provides a pyrimidone of the formula IX. When $R^5$ is an acetate group, the foregoing reaction provides a mixture of pyrimidones of the formulae VIII and IX. The foregoing reaction is carried out in an aprotic solvent (e.g., dimethylformamide) at a temperature of about 25° to about 150° C., preferably about 100° C., for about 1 to about 48 hours, preferably about 24 hours.

Although both the compound of the formula VIII and the compound of the formula IX may be reacted with an activated ester to prepare a compound of the formula I (via an intermediate of the formula XII or XI, respectively) as described below, it is, generally, convenient to convert the compound of the formula VIII to the compound of the formula IX, before reacting the latter with the activated ester.

In order to convert the compound of the formula VIII to a compound of the formula IX, the compound of the formula XIII is treated with a reagent capable of introducing the $R^5$ protecting group. For example, the compound of the formula VIII may be reacted with acetic anhydride and a base (e.g., pyridine or triethylamine), with or without an added solvent (e.g., methylene chloride), at a temperature of about −20° to about 50° C., preferably about 25° C., to obtain the compound of the formula IX.

The compound of the formula IX or the compound of the formula VIII, or the mixture of the formula IX and the compound of the formula VIII, is reacted with an activated ester of the formula X, wherein $R^6$ is hydrogen, ($C_1$-$C_{14}$)alkyl, $C_2$-$C_{14}$(alkenyl), ($C_6$-$C_9$)phenylalkyl, or substituted ($C_6$-$C_{19}$)phenylalkyl, and wherein the substituents on the substituted phenylalkyl are independently one or two of fluoro, chloro, ($C_1$-$C_3$)alkyl, ($C_1$-$C_3$)alkoxy and trifluoromethyl, and the group X is chloro or bromo, preferably chloro, in an aprotic solvent (preferably methylene chloride or pyridine) at about −20° to about 100° C. (preferably about 0° C.) for about 0.5 to about 24 hours (preferably about 18 hours) with a base catalyst (preferably, dimethylaminopyridine). As a result, there is formed, respectively, the compound of the formula XI, the compound of the formula XII, or a mixture of the compound of the formula XI and the compound of the formula XII.

The compound of the formula XI or the compound of the formula XII may be reduced with a hydride reducing agent (e.g., diborane) in an anhydrous solvent (preferably tetrahydrofuran) for about 1 to about 24 hours (preferably about 18 hours) at about 0° to about 50° C. (preferably about 25° C.) to prepare the compound of the formula I. If reduction of the group

to form an $R^2$ group does not also deprotect the $R^5$ groups in the compound of the formula XI (such as occurs when $R^5$ is acyl), a further deprotecting step (e.g., hydrogenation when $R^5$ is benzyl or treatment with aqueous acid when $R^5$ is tetrahydropyranyl) provides the compound of the formula I.

The compound of the formula IX may also be deprotected to provide the compound of the formula I. When $R^5$ is

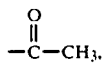

deprotection is effected by hydrolysis; when $R^5$ is tetrahydropyranyl, deprotection is effected by treatment with aqueous acid; and when $R^5$ is

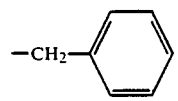

deprotection is effected by hydrogenation.

Acid addition salts of the compounds of formula I are prepared in a conventional manner by treating a solution or suspension of the free base of a compound of the formula I with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic such as methanesulfonic, benzenesulfonic, and related acids. Preferably, the acid is phosphoric acid.

Base addition salts of compounds of the formula I may be prepared in a conventional manner by reacting a compound of the formula I with about one chemical equivalent of inorganic base such as an alkali metal hydroxide or an alkaline earth metal hydroxide.

The activity of the compounds of formula I and their salts in the treatment of pulmonary, asthmatic, allergic and inflammatory diseases may be determined by a standard test measuring an agent's ability to inhibit cyclooxygenase and 5-lipoxygenase enzyme activity of rat basophil leukemia 5-(RBL-1) cells. According to this test as described by Jakschick et al., *Prostaglandins*, 16, 733–747 (1978), a monolayer of RBL-1 cells is grown for 1 or 2 days in spinner culture in Eagle's minimum essential medium, 15% heat-inactivated fetal calf serum and an antibiotic/antimycotic mixture. The cells are washed after centrifugation and incubated in a buffer. A volume of 0.5 ml of cell suspension is preincubated at 30° C. for ten minutes with a 1 microliter dimethylsulfoxide (DMSO) solution of the agent to be tested. The incubation is initiated by simultaneous addition of 5 microliters of ($^{14}$C)arachidonic acid in ethanol and 2 microliters calcium ionophore (A-21387) in DMSO for final concentrations of 5 and 7.6 micromolar, respectively. Five minutes later, the incubation is terminated by the addition of 0.27 ml acetonitrile/acetic acid (100:3). High pressure liquid chromatography is performed using acetonitrile/water/acetic acid solvent. Radiolabeled prostaglandin $D_2$($PGD_2$), leukotriene $B_4$($LTB_4$), 5-hydroxyeicosatetraenoic acid (5-HETE), and unreacted arachidonic acid are determined. The inhibitory effect on the cyclooxygenase pathway is assessed from the reduction of $PGD_2$ levels and the inhibitory effect on the 5-lipoxygenase pathway is assessed from the decrease in the amount of $LTB_4$ and 5-HETE.

The compounds of the formula I and their pharmaceutically acceptable salts are effective inhibitors of mammalian leukotriene biosynthesis in mammals and are thus useful in the treatment of various leukotriene mediated conditions. In particular, the compounds have utility, both as the sole active agent and also in combination with other active agents, for the treatment of various pulmonary, gastrointestinal, inflammatory, dermatological and cardiovascular conditions such as inflammation, arthritis, allergy, psoriasis, asthma, bronchitis, pulmonary hypertension and hypoxia, peptic ulcers, inflammatory bowel disease or cardiovascular spasm, such as acute myocardial infarctions, and the like in mammals, especially in humans.

For treatment of the various conditions described above, the compounds of formula I and their pharmaceutically acceptable salts may be administered to a subject in need of treatment by a variety of conventional routes of administration, including oral, by injection, topical, and in an aerosol carrier composition for administration by inhalation.

The exact dosage of a compound of the present invention will depend upon such factors as the age, weight and condition of the patient and the severity of disease. In general, however, a therapeutically-effective dose of a compound of formula I or a pharmaceutically acceptable salt thereof will range from 0.01 to 100 mg/kg body weight of the subject to be treated per day, preferably 0.1 to 50 mg/kg per day.

Although the compounds of formula I and their salts can be administered alone, they will generally be administered in admixture with a pharmaceutical carrier selected with regard to the intended route of administration and standard pharmaceutical practice. For example, oral administration may be in the form of tablets containing such excipients as starch or lactose, or in the form of elixirs or suspensions containing flavoring or coloring agents. In the case of animals, they are advantageously contained in an animal feed or drinking water. For parenteral injection, they may be used in the form of a sterile aqueous solution which may contain other solutes, for example enough salt or glucose to make the solution isotonic. Other active compounds, including NSAIDS (non-steroidal antiinflammatory drugs) may be administered along with the compounds of the present invention.

The following non-limiting Examples are illustrative of the compounds of the present invention. All melting points referred to in the Examples are uncorrected.

EXAMPLE 1

2-Heptylamino-5-hydroxy-6-methyl-4-pyrimidone

A. 5-Acetoxy-2-amino-6-methyl-4-pyrimidone

2-Amino-5-hydroxy-6-methyl-4-pyrimidone (0.88 g, prepared as described in Hüll, *J. Chem. Soc.*, 2033 (1956)), was treated with pyridine (5 ml) and acetic anhydride (0.5 ml) at 0° C. The reaction mixture was stirred at 25° C. for 18 hours. Filtration provided a white solid (0.64 g). Recrystallization (absolute ethanol) afforded a white crystalline solid (m.p.: 273°–276° C.).

B. 2-Heptylamino-5-hydroxy-6-methyl-4-pyrimidone

A sample prepared as above (1.83 g, 10 mmol) in pyridine (25 ml) was cooled 0° C. under $N_2$ and treated with 4-dimethylaminopyridine (1.6 g) followed by the dropwise addition of heptanoyl chloride (1.9 g, 10 mmol) in methylene chloride (10 ml). Aqueous extractive work up gave a crude product which was used directly. This product (0.5 g, 1.7 mmol) was dissolved in dry tetrahydrofuran (THF) (10 ml) and treated with borane-THF (1M, 8 ml). The reaction mixture was stirred overnight and was then quenched with methanol (10 ml) and concentrated on a rotary evaporator. The residue was refluxed in 20 ml of 6N HCl for 2 hours. The cooled reaction mixture was filtered, providing a white crystalline product (m.p.: 233°–235° C.).

EXAMPLE 2

2-(6-Methylheptyl-2-amino)-5-hydroxy-4-pyrimidone

A. 2-N-Guanidino-6-methylheptane Acetate 3,5-Dimethylpyrazole-1-carboxamidine (10 g, 0.07 mol), 2-amino-6-methylheptane (9.33 g, 0.07 mol) and acetic acid (4.5 ml) were combined and heated under reflux for 96 hours. The reaction mixture was cooled and filtered, yielding a white solid (12.6 g, 82%) m.p. 148°–152° C.

B. 2-(6-Methylheptyl-2-amino)-5,5-diethoxy-6H-4-pyrimidone

The above N-alkyl guanidine (5.75 g, 25 mmol) was treated with freshly prepared sodium ethoxide (25 mmol) at 25° C. for 1 hour under $N_2$. The reaction was filtered and the filtrate was added to a solution (50 ml ethanol) of 4-nitrophenyl 3-bromo-2,2-diethoxypropionate (3.0 g, 8.3 mmol). The reaction mixture was heated under reflux for 24 hours and was then cooled and concentrated. The residue was dissolved in ethyl acetate (100 ml) and extracted with 20% sodium carbonate (2×50 ml). The organic layer was dried (sodium sulfate) and concentrated, yielding 1.91 g (74%) of crude product. Chromatography (silca gel, 10:1, chloroform:methanol as eluent) and recrystallization (acetonitrile) afforded an analytically pure sample, m.p. 170°–172° C. Anal. Calcd. for $C_{16}H_{33}N_3O_4$: C, 60.81; H, 9.99; N, 13.41. Found: C, 60.44; H, 9.98; N, 13.21.

C.

2-(6-Methylheptyl-2-amino)-5-hydroxy-4-pyrimidone

The above compound (1.0 g, 3.2 mmol) was heated under reflux in formic acid (50 ml) for 24 hours. The reaction mixture was then cooled and concentrated. Chromatography on silica gel (chloroform:methanol, 20:1) afforded a solid (0.26 g, 34%) m.p. 95°–100° C. Trituration of the solid with ethanol and recrystallization (acetonitrile) afforded an analytically pure sample. Anal. Calcd. for $C_{12}H_{21}N_3O_2$: C, 60.22; H, 8.84; N, 17.56. Found: C, 59.78; H, 8.95; N, 17.31.

EXAMPLE 3

The following compounds were prepared using, as indicated below, a method similar to that set forth in Example 1 or 2:

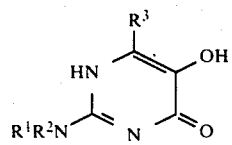

| $R^1$ | $R^2$ | $R^3$ | m.p. | Example |
|---|---|---|---|---|
| $(CH_2)_5CH_3$ | H | H | 237–240° C. | 1 |
| $(CH_2)_6CH_3$ | H | $CH_3$ | 233–235° C. | 1 |
| $CH_3(CH)CH_2CH_2Ph$ | H | H | 125–126° C. | 2 |
| $CH_2Ph$ | H | H | 210–215° C. | 1 |
| $CH_3(CH)(CH_2)_3CH(CH_3)_2$ | H | H | 95–100° C. | 2 |

Ph = phenyl

EXAMPLE 4

Using the method of Jakschick et al. described above, the title compounds of Example 1 and 2 and the compounds of Example 3 were tested for their ability to inhibit lipoxygenase enzyme.

All of the compounds were active at a level of 20 micromolar.

We claim:

1. A compound of the formula or a pharmaceutically acceptable salt thereof, wherein $R^1$ is hydrogen; $R^2$ is $(C_2–C_{15})$alkyl, $(C_3–C_{15})$alkenyl, phenyl, substituted phenyl, $(C_7–C_{20})$phenylalkyl, or substituted $(C_7–C_{20})$phenylalkyl, wherein the substituents on the substituted phenyl and substituted phenylalkyl are independently one or two of fluoro, chloro, $(C_1-C_3)$alkyl, $(C_1-C_3)$alkoxy, and trifluoromethyl; or $R^1$ and $R^2$ together with the nitrogen atom to which they are attached form a pyrrolidinyl, substituted pyrrolidinyl, piperidyl or substituted piperidyl group, wherein the substituents on said substituted pyrrolidinyl and piperidyl groups are independently one of $(C_1-C_6)$alkyl, phenyl, and $(C_7-C_9)$phenylalkyl; and $R^3$ is hydrogen, $(C_1-C_6)$alkyl, phenyl, substituted phenyl, $(C_7-C_9)$phenylalkyl, or substituted $(C_7-C_9)$phenylalkyl, wherein the substituents on the substituted phenyl and substituted phenylalkyl are independently one or two of fluoro, chloro, $(C_1-C_3)$alkyl, $(C_1-C_3)$alkoxy, and trifluoromethyl.

2. A compound according to claim 1, wherein $R^1$ is hydrogen, $R^2$ is linear or branched $(C_2-C_{15})$alkyl or $(C_7-C_{20})$phenylalkyl wherein the alkyl moiety is linear or branched; and $R^3$ is hydrogen or methyl.

3. A compound according to claim 1, wherein $R^2$ is cyclopentyl or cyclohexyl.

4. A compound according to claim 1, said compound being selected from the group consisting of
2-heptylamino-5-hydroxy-6-methyl-4-pyrimidone;
2-(6-methylheptyl-2-amino)-5-hydroxy-4-pyrimidone;
2-[(1-methyl-3-phenyl)-propyl]amino-5-hydroxy-4-pyrimidone; and
2-benzylamino-5-hydroxy-4-pyrimidone.

5. A pharmaceutical composition for the treatmet of leukotriene mediated pulmonary, asthmatic, allergic, cardiovascular, gastrointestinal, or inflammatory diseases which comprises a compound according to claim 1 in an amount effective for the treatment of any one of said diseases in admixture with a pharmaceutically acceptable carrier.

6. A composition according to claim 5, wherein said diseases are arthritis asthma, psoriasis, bronchitis, pulmonary hypertension, pulmonary hypoxia, peptic ulcers, inflammatory bowel disease or cardiovascular spasm.

7. A method for the treatment of leukotriene mediated pulmonary, asthmatic, allergic, cardiovascular, gastrointestinal, or inflammatory diseases which comprises administering to a host in need of such treatment an amount of a compound according to claim 1 effective in treating any one of said diseases.

8. A method according to claim 7, wherein said diseases are arthritis asthma, psoriasis, bronchitis, pulmonary hypertension, pulmonary hypoxia, peptic ulcers, inflammatory bowel disease or cardiovascular spasm.

9. A composition according to claim 5, wherein $R^1$ is hydrogen, $R^2$ is linear or branched $(C_2-C_{15})$alkyl or $(C_7-C_{20})$phenylalkyl wherein the alkyl moiety is linear or branched; and $R^3$ is hydrogen or methyl.

10. A composition according to claim 5, wherein $R^2$ is cyclopentyl or cyclohexyl.

11. A composition according to claim 5, said compound being selected from the group consisting of:
2-heptylamino-5-hydroxy-6-methyl-4-pyrimidone;
2-(6-methylheptyl-2-amino)-5-hydroxy-4-pyrimidone;
2-[(1-methyl-3-phenyl)-propyl]amino-5-hydroxy-4-pyrimidone; and
2-benzylamino-5-hydroxy-4-pyrimidone.

12. A composition according to claim 9 wherein said diseases are arthritis asthma, psoriasis, bronchitis, pulmonary hypertension, pulmonary hypoxia, peptic ulcers, inflammatory bowel disease or cardiovascular spasm.

13. A composition according to claim 10, wherein said diseases are arthritis asthma, psoriasis, bronchitis, pulmonary hypertension, pulmonary hypoxia, peptic ulcers, inflammatory bowel disease or cardiovascular spasm.

14. A composition according to claim 11, wherein said diseases are arthritis asthma, psoriasis, bronchitis, pulmonary hypertension, pulmonary hypoxia, peptic ulcers, inflammatory bowel disease or cardiovascular spasm.

15. A method according to claim 7, wherein $R^1$ is hydrogen, $R^2$ is linear or branched $(C_2-C_{15})$alkyl or $(C_7-C_{20})$phenylalkyl wherein the alkyl moiety is linear or branched; and $R^3$ is hydrogen or methyl.

16. A methyl according to claim 7, wherein $R^2$ is cyclopentyl or cyclohexyl.

17. A method according to claim 7, said compound being selected from the group consisting of:
2-heptylamino-5-hydroxy-6-methyl-4-pyrimidone;
2-(6-methylheptyl-2-amino)-5-hydroxy-4-pyrimidone;
2-[(1-methyl-3-phenyl)-propyl]amino-5-hydroxy-4-pyrimidone; and
2-benzylamino-5-hydroxy-4-pyrimidone.

18. A method according to claim 15, wherein said diseases are arthritis asthma, psoriasis, bronchitis, pulmonary hypertension, pulmonary hypoxia, peptic ulcers, inflammatory bowel disease or cardiovascular spasm.

19. A method according to claim 16, wherein said diseases are arthritis asthma, psoriasis, bronchitis, pulmonary hypertension, pulmonary hypoxia, peptic ulcers, inflammatory bowel disease or cardiovascular spasm.

20. A method according to claim 17, wherein said diseases are arthritis asthma, bronchitis, pulmonary hypertension, pulmonary hypoxia, peptic ulcers, inflammatory bowel disease or cardiovascular spasm.

21. A compound according to claim 1, wherein $R^1$ is hydrogen, $R^2$ is linear or branched $(C_5-C_{15})$ alkyl or $(C_7-C_{20})$ phenylalkyl wherein the alkyl moiety is linear or branched; and $R^3$ is hydrogen or methyl.

22. A compound according to claim 21, wherein $R^2$ is linear or branched $(C_5-C_8)$ alkyl.

23. A method of inhibiting leukotriene bio-synthesis in a mammal comprising administering to a mammal a leukotriene bio-synthesis inhibiting amount of a compound according to claim 1.

24. A method according to claim 23 wherein said compound is a compound wherein $R^1$ is hydrogen, $R^2$ is linear or branched $(C_5-C_{15})$ alkyl or $(C_7-C_{20})$ phenylalkyl wherein the alkyl moiety is linear or branched; and $R^3$ is hydrogen or methyl.

25. A methyl according to claim 7 wherein said diseases are pulmonary, asthmatic, allergic, cardiovascular or inflammatory diseases.

26. A composition according to claim 5, wherein $R^1$ is hydrogen, $R^1$ linear or branched $(C_5-C_{15})$ alkyl or $(C_7-C_{20})$ phenylalkyl wherein the alkyl moiety is linear or branched; and $R^3$ is hydrogen or methyl.

* * * * *